United States Patent
Biedermann et al.

(10) Patent No.: US 9,333,011 B2
(45) Date of Patent: May 10, 2016

(54) POLYAXIAL BONE ANCHORING DEVICE

(75) Inventors: Lutz Biedermann, VS-Villingen (DE);
Wilfried Matthis, Weisweil (DE);
Michael Kegel, Tennenbronn (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 13/338,188

(22) Filed: Dec. 27, 2011

(65) Prior Publication Data

US 2012/0165882 A1     Jun. 28, 2012

Related U.S. Application Data

(60) Provisional application No. 61/427,412, filed on Dec. 27, 2010.

(30) Foreign Application Priority Data

Dec. 27, 2010    (EP) .................................... 10197083

(51) Int. Cl.
*A61B 17/04*       (2006.01)
*A61B 17/84*       (2006.01)
*A61F 2/08*        (2006.01)
*A61B 17/70*       (2006.01)

(52) U.S. Cl.
CPC .................................. *A61B 17/7037* (2013.01)

(58) Field of Classification Search
CPC ........... A61B 17/7037; A61B 17/7035; A61B 17/7032; A61B 17/7034
USPC ................... 606/300–321, 264–275
See application file for complete search history.

(56) References Cited

U.S. PATENT DOCUMENTS

| | | | |
|---|---|---|---|
| 5,681,319 A | 10/1997 | Biedermann et al. | |
| 6,113,601 A | 9/2000 | Tatar | |

(Continued)

FOREIGN PATENT DOCUMENTS

| | | |
|---|---|---|
| EP | 1 222 899 A2 | 7/2002 |
| EP | 2 221 012 A1 | 8/2010 |

(Continued)

OTHER PUBLICATIONS

Extended European Search Report for European Application No. 10197083.8, extended European Search Report dated May 26, 2011 and mailed Jun. 8, 2011 (10 pgs.).

*Primary Examiner* — Kevin T Truong
*Assistant Examiner* — Si Ming Ku
(74) *Attorney, Agent, or Firm* — Lewis Roca Rothgerber Christie LLP (57) ABSTRACT

A polyaxial bone anchoring device includes an anchoring element having a shaft and a head having a curved outer surface portion; a receiving part having a top end and a bottom end, a coaxial bore extending from the top end in the direction of the bottom end, and a seat portion for receiving the head at the bottom end; and a pressure element having a head contacting surface portion that contacts the curved outer surface portion of the head; wherein the head is pivotable with respect to the receiving part and can be fixed at an angle by exerting pressure via the pressure element, and wherein the head has an oversize in the curved outer surface portion with respect to the head contacting surface portion, such that an interference fit is achieved that clamps the head by the friction between the outer surface portion and the head contacting surface portion.

19 Claims, 6 Drawing Sheets

(56) References Cited

U.S. PATENT DOCUMENTS

| | | |
|---|---|---|
| 6,355,040 B1 | 3/2002 | Richelsoph et al. |
| 6,471,705 B1 | 10/2002 | Biedermann et al. |
| 7,087,057 B2* | 8/2006 | Konieczynski et al. ...... 606/278 |
| 7,604,655 B2 | 10/2009 | Warnick |
| 7,604,656 B2 | 10/2009 | Shluzas |
| 7,682,377 B2 | 3/2010 | Konieczynski et al. |
| 8,506,609 B2 | 8/2013 | Biedermann et al. |
| 8,764,810 B2 | 7/2014 | Biedermann et al. |
| 8,926,671 B2 | 1/2015 | Biedermann et al. |
| 8,940,024 B2 | 1/2015 | Biedermann et al. |
| 9,155,568 B2 | 10/2015 | Biedermann et al. |
| 9,192,413 B2 | 11/2015 | Biedermann et al. |
| 2003/0167058 A1 | 9/2003 | Shluzas |
| 2004/0267264 A1 | 12/2004 | Konieczynski et al. |
| 2005/0154391 A1 | 7/2005 | Doherty et al. |
| 2007/0118117 A1 | 5/2007 | Altarac et al. |
| 2007/0161996 A1* | 7/2007 | Biedermann et al. ........... 606/61 |
| 2008/0045953 A1 | 2/2008 | Garamszegi |
| 2008/0154315 A1 | 6/2008 | Jackson |
| 2008/0269809 A1 | 10/2008 | Garamszegi |
| 2009/0062865 A1* | 3/2009 | Schumacher ................. 606/301 |
| 2010/0145394 A1 | 6/2010 | Harvey et al. |
| 2010/0152787 A1* | 6/2010 | Walsh et al. .................. 606/308 |
| 2010/0152788 A1 | 6/2010 | Warnick |
| 2010/0160980 A1* | 6/2010 | Walsh et al. .................. 606/308 |
| 2012/0143260 A1* | 6/2012 | Gunn et al. .................... 606/302 |
| 2012/0165881 A1 | 6/2012 | Biedermann et al. |
| 2013/0165977 A1 | 6/2013 | Biedermann et al. |

FOREIGN PATENT DOCUMENTS

| | | |
|---|---|---|
| JP | 2002-233532 A | 8/2002 |
| WO | WO 2009/014540 A1 | 1/2009 |
| WO | WO 2009/055747 A1 | 4/2009 |

* cited by examiner

POLYAXIAL BONE ANCHORING DEVICE

CROSS-REFERENCE TO RELATED APPLICATIONS

The present application claims the benefit of U.S. Provisional Patent Application Ser. No. 61/427,412, filed Dec. 27, 2010, the contents of which are hereby incorporated by reference in its entirety, and claims priority to European Patent Application EP 10 197 083.8, filed Dec. 27, 2010, the contents of which are hereby incorporated by reference in its entirety.

The invention relates to a polyaxial bone anchoring device for anchoring a stabilization rod in a bone or in a vertebra. The bone anchoring device includes an anchoring element, a receiving part for receiving a head of the bone anchoring element and for receiving a stabilization rod to be connected to the anchoring element. The anchoring element is pivotably connected to the receiving part and can be fixed at an angle by exerting pressure onto the head via a pressure element which is arranged in the receiving part. The pressure element comprises a head contacting surface that contacts the head. The head is slightly oversized with respect to the head contacting surface to achieve an interference fit such that the head is clamped by friction before it is locked.

US 2004/0267264 A1 describes a polyaxial fixation device wherein the polyaxial bone screw includes an engagement member that is adapted to provide sufficient friction between the spherical head and the receiver member to enable the shank to be maintained in a desired angular orientation before locking the spherical head within the receiver member. The engagement member is realized, for example, by an open snap ring around the head or by spring members provided at the compression cap to frictionally engage the spherical head or by a slot provided in the compression cap.

It is an object of the invention to provide a bone anchoring device which allows an improved handling during surgery while ensuring safe fixation.

With the bone anchoring device a temporary clamping of the head in a desired angular position with respect to the receiving part without locking the head can be achieved. This allows to maintain the receiving part in an adjustable angular position. In this condition, the pressure element exerts a pre-load onto the head wherein the head is not locked but prevented from freely pivoting. When the head is temporarily clamped, the alignment of the receiving part with respect to the rod and the insertion of the rod is facilitated, in particular in a situation in which a multitude of bone anchors have to be connected to the rod. When the rod is already inserted into the receiving part, adjustments of the rod are still possible without completely loosening the head.

The amount of preload exerted onto the head by the pressure member can be exactly predefined by dimensioning the size of the pressure member with respect to the head in view of the interference fit between the pressure member and the head.

The head may be secured in the seat. This enables an easy assembly of the device without additional crimp tools.

Further features and advantages of the invention will become apparent from the description of embodiments by means of the accompanying drawings.

Figure 1:
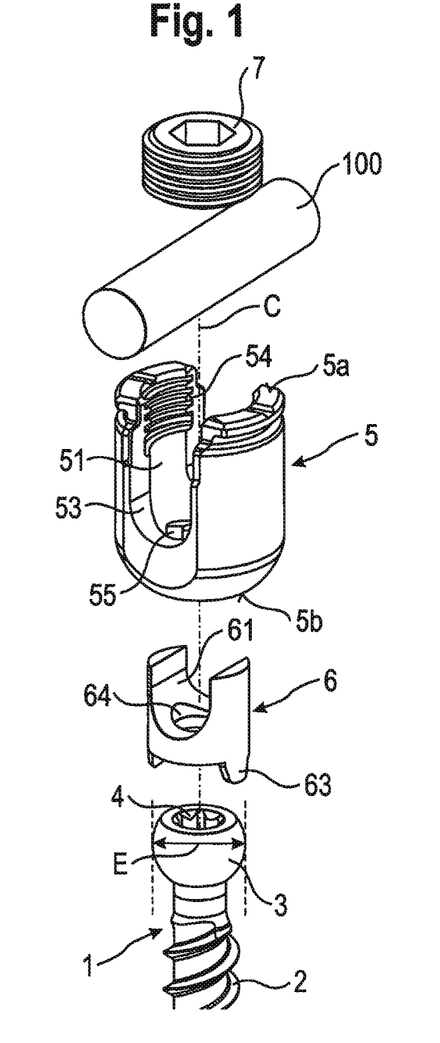
FIG. 1 shows a perspective exploded view of the polyaxial bone anchoring device according to a first embodiment.
Figure 2:
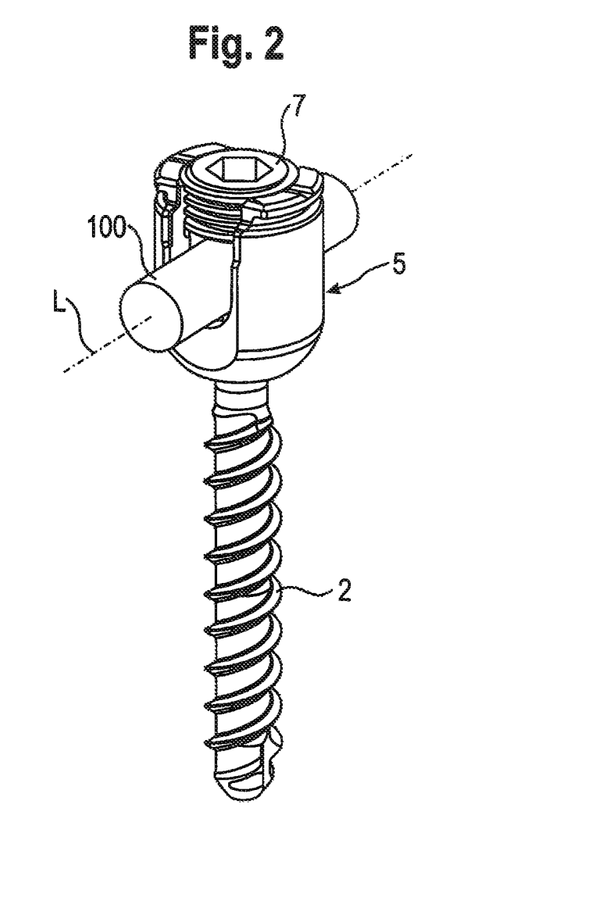
FIG. 2 shows a perspective view of the bone anchoring device in an assembled state.
Figure 3:
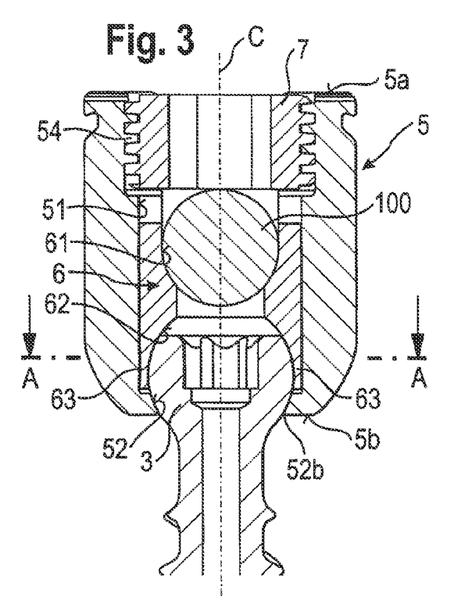
FIG. 3 shows a cross-sectional view of the polyaxial bone anchoring device in the assembled state, the cross-section being taken in a plane perpendicular to the rod axis.
Figure 4:
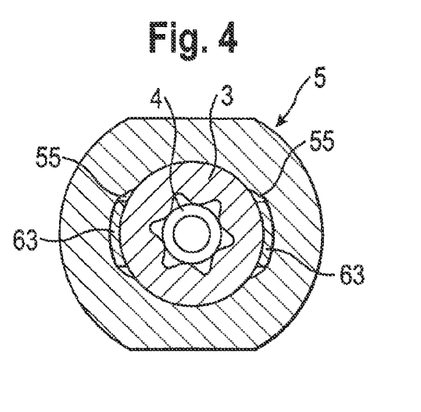
FIG. 4 shows a cross-sectional view of the bone anchoring device along line A-A in FIG. 3.
Figure 5:
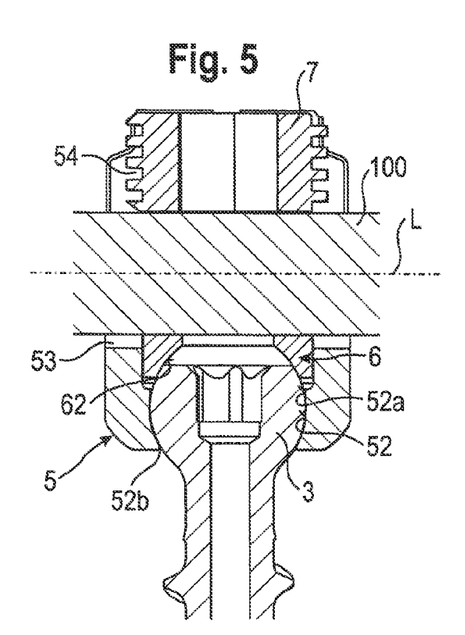
FIG. 5 shows a cross-sectional view of the bone device in the assembled state, the cross-section taken in a plane including the rod axis.

The polyaxial bone anchoring device according to a first embodiment which is generally shown in FIGS. 1 and 2 includes a bone anchoring element 1 in the form of a screw member having a threaded shaft 2 and a head 3. The head 3 is shaped as a spherical segment that has a size including the equator or largest diameter E of the sphere. On its free end the head 3 has a recess 4 for engagement with a tool. The bone anchoring device further includes a receiving part 5 for connecting the screw member 1 to a rod 100. A pressure element 6 is arranged in the receiving part on top of the head 3. For securing the rod 100 in the receiving part and for exerting pressure onto the head a locking device in the form of an inner screw 7 which cooperates with the receiving part 5 is provided.

Figure 6:
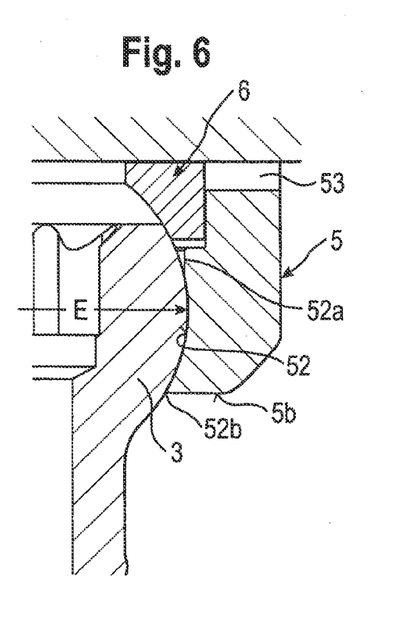
FIG. 6 shows an enlarged view of a portion of FIG. 5.

As shown in particular in FIGS. 3 to 10, the receiving part 5 is substantially cylindrical and has a top end 5a and a bottom end 5b and a coaxial bore 51 extending towards the bottom end 5b. At the bottom end 5b, a seat portion 52 is provided for accommodating the head 3. The seat portion 52 is spherically-shaped with a radius corresponding to the radius of the head 3 and has an opening 52b through which the shaft can extend. It allows the head 3 to pivot in the seat portion 52 similar to a ball and socket joint. The height of the seat portion 52 is such that the seat portion 52 includes the region of the head 3 with the largest diameter E, as shown in FIG. 6.

Between the bore 51 and the seat portion 52 a hollow cylindrical edge portion 52a is provided that has an inner diameter that is smaller than that of bore 51 and only slightly smaller than the greatest outer diameter E of the head. In other words, the head 3 has a slight oversize with respect to the cylindrical edge portion 52a to allow the head to be pushed through the edge portion into the seat. Hence, once the head 3 has been introduced into the seat portion 52 it is held by the cylindrical edge portion 52a within the seat portion.

At the top end 5a the receiving part has a substantially U-shaped recess 53 that forms a channel for receiving the rod 100. By means of the U-shaped recess a channel axis L is formed that extends perpendicular to a central axis C of the receiving part 5. An internal thread 54 is provided at the receiving part adjacent the top end 5a for cooperating with the inner screw 7 of the locking device.

Figure 7:
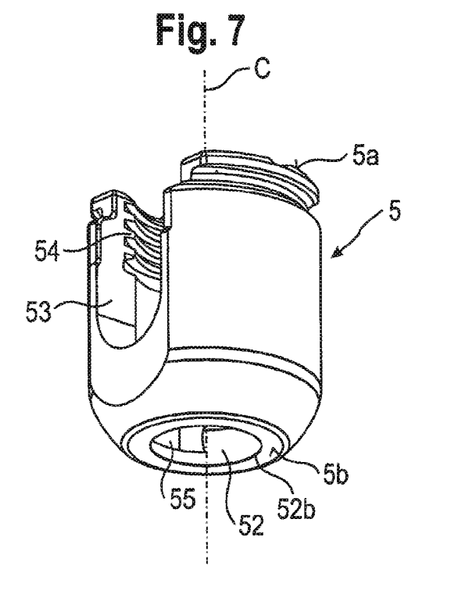
FIG. 7 shows a perspective view of the receiving part of the polyaxial bone anchoring device.
Figure 8:
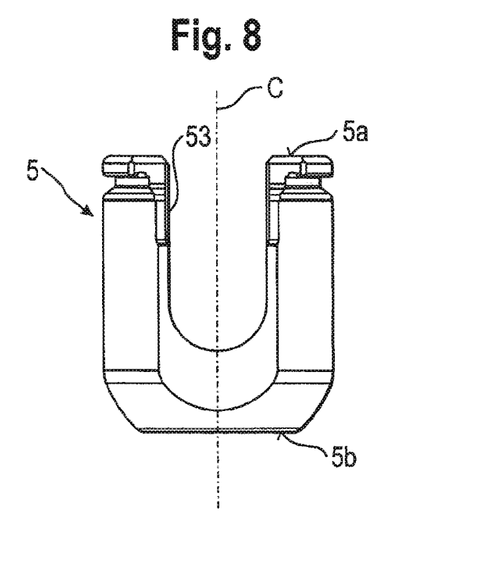
FIG. 8 shows a side view of the receiving part of FIG. 7.
Figure 9:
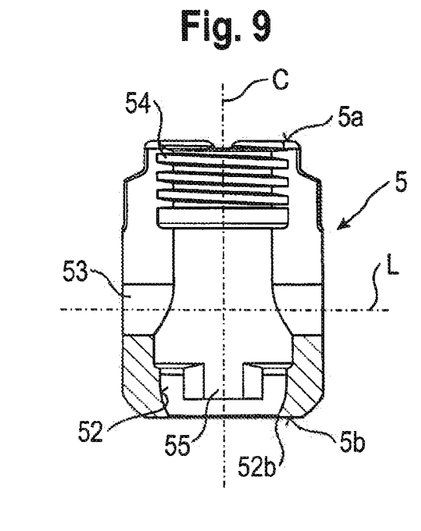
FIG. 9 shows a cross-sectional view of the receiving part, the section being taken in a plane including the rod axis.
Figure 10:
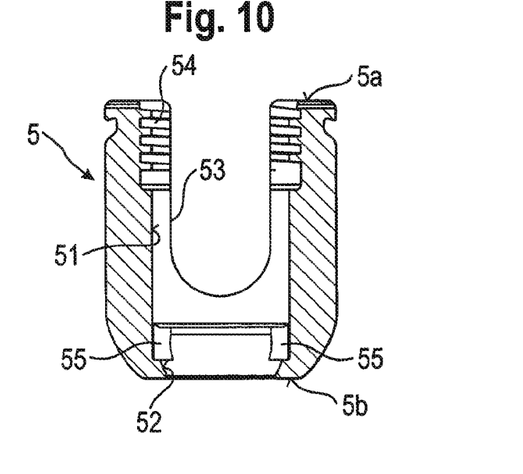
FIG. 10 shows a cross-sectional view of the receiving part, the section being taken in a plane perpendicular to the rod axis.
Figure 11:
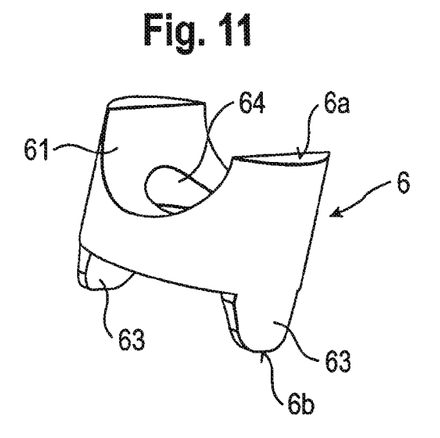
FIG. 11 shows a perspective view of the pressure element.
Figure 12:
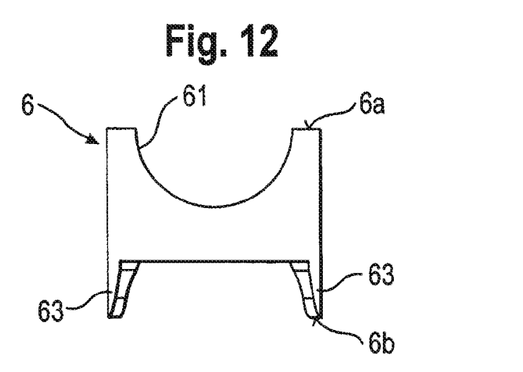
FIG. 12 shows a side view of the pressure element.

As can be seen particular in FIGS. 7, 9 and 10, two recesses 55 that are arranged at 180° offset from each other are provided that extend from the bore 51 to a distance from the bottom end 5b into the seat portion 52. The recesses 55 are located at 90° with respect to the channel axis L. The shape of the recesses 55 is configured to accommodate a portion of the pressure element 6 to be described below.

Figure 13:
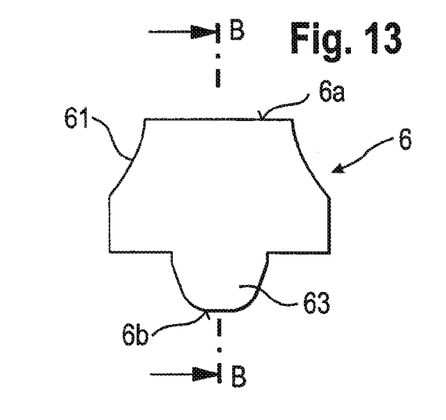
FIG. 13 shows a side view of the pressure element of FIG. 12 rotated by 90°.
Figure 14:
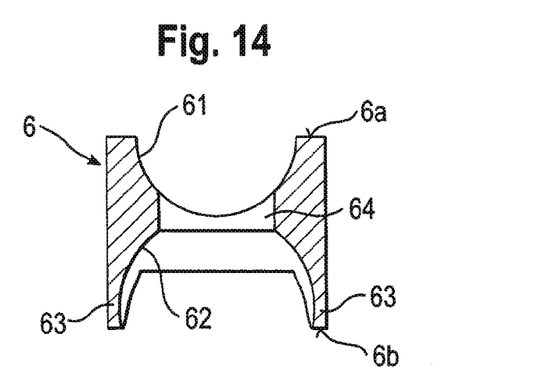
FIG. 14 shows a cross-sectional view of the pressure element along line B-B in FIG. 13.
Figure 15:
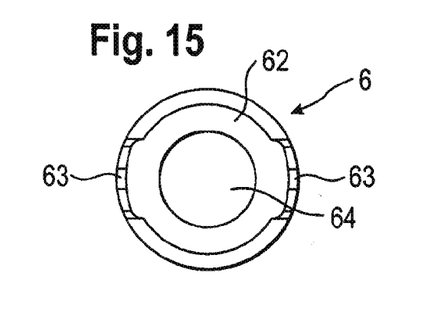
FIG. 15 shows a bottom view of the pressure element of FIG. 11.

The pressure element 6 is formed in one piece. It is of substantially cylindrical construction and has an outer diameter which allows it to move in the axial direction within the bore 51 of the receiving part 5. The pressure element has a top end 6a and a bottom end 6b. At the top end 6a a cylindrical recess 61 is provided which is configured to receive the rod 100 therein. At the bottom end 6b a spherical recess 62 is provided for receiving the head 3 therein. At the bottom end 6b there are two opposing cut-outs in a circumferential direction by means of which two downwardly extending opposing lugs 63 are provided, the inner surface of which is spherically shaped and the outer surface of which is cylindrical. The lugs 63 have an approximate V-shape seen in the side view, as for example shown in FIG. 13, wherein the corners are rounded and the bottom is straight. However, the shape of the lugs is not restricted to the shape shown in the embodiment. For example, it can be rectangular or U-shaped or otherwise shaped. The lugs 63 are arranged at 90° with respect to the channel axis formed by the cylindrical recess. The depth of the spherical recess 62 is such that the lugs 63 extend beyond the area with the greatest outer diameter E of the spherical head 3 when the pressure element is mounted onto the head 3.

The size of the spherical recess 62 with respect to the spherical head 3 is such that the head 3 has a slight oversize with respect to the spherical recess 62 such that when the spherical head 3 is inserted into the spherical recess 62 an interference fit is achieved that holds the head by frictional forces exerted by the lugs 63 onto the head. The strength of the frictional forces can be adjusted by designing an appropriate interference fit between the head and the spherical recess 62 with the lugs 63.

Furthermore, the pressure element 6 has a coaxial bore 64 for allowing access to the screw head 3 with a tool (not shown).

All parts of the bone anchoring device are made of a body-compatible material, such as a body-compatible metal, for example, titanium, body-compatible metal alloys such as, for example, Nitinol or from a body-compatible plastic material, such as, for example, polyetheretherketone (PEEK) or combinations thereof. The parts can be made of the same or of different materials.

Figure 16A:
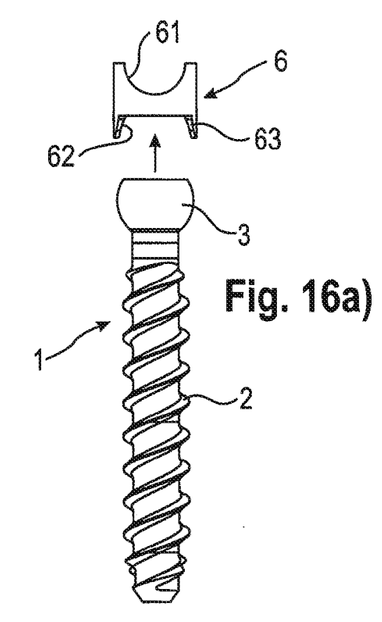
FIGS. 16a) to 16d) show steps of assembly of the polyaxial bone anchoring device.
Figure 16B:
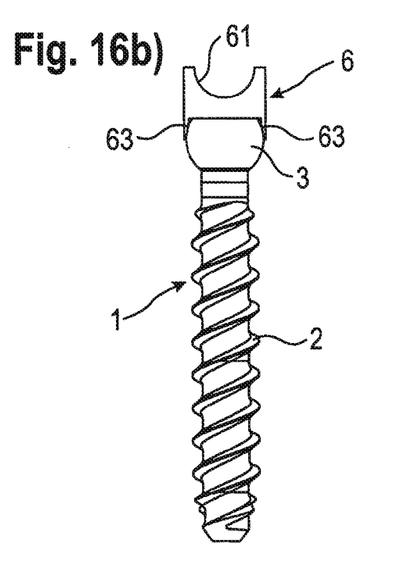

The assembly of the bone anchoring device will now be described with reference to FIGS. 16a) to 16d). First, as shown in FIG. 16a) the head 3 of the bone anchoring device is introduced into the spherical recess 62 of the pressure element 6. Since the head 3 has a slightly greater diameter than the diameter of the spherical recess 62 the head 3 is held by an interference fit within the spherical recess 62 as shown in FIG. 16b). Thereby, the lugs 63 extend around the head beyond the region with the largest diameter E. In this condition, the head can be pivoted with respect to the pressure element 6 by applying a force to overcome the friction force between the head and the lugs 63.

Then, the screw element 1 with the mounted pressure element is introduced into the receiving part 5 from the top end 5a. Thereby, the pressure element 6 is oriented such that its cylindrical recess 61 is aligned with the U-shaped recess 53 of the receiving part. Therefore, the lugs 63 are oriented such that they can engage the recesses 55 of the receiving part as previously shown in FIG. 7. Finally, as shown in FIG. 16d) the head 3 is inserted into the seat portion 52 by overcoming the force inserted through the interference fit between the upper cylindrical edge 52a of the seat portion and the head 3.

When the head 3 with the pressure element 6 is mounted within the receiving part 5, the head 3 is held by the friction forces exerted by the lugs 63 onto the head. Further, since the head 3 is held in the seat portion 52 by the cylindrical upper edge 52a of the seat portion, the head is temporarily held in the receiving part in an adjustable angular position. No additional fixation of the pressure element, such as crimping, is necessary since the pressure element is secured against rotation by the engagement of the lugs 63 in the recesses 55 and against escape through the open top end by the interference fit with the head which itself is held by the upper edge 52a in the seat portion.

Figures 16C, 16D:
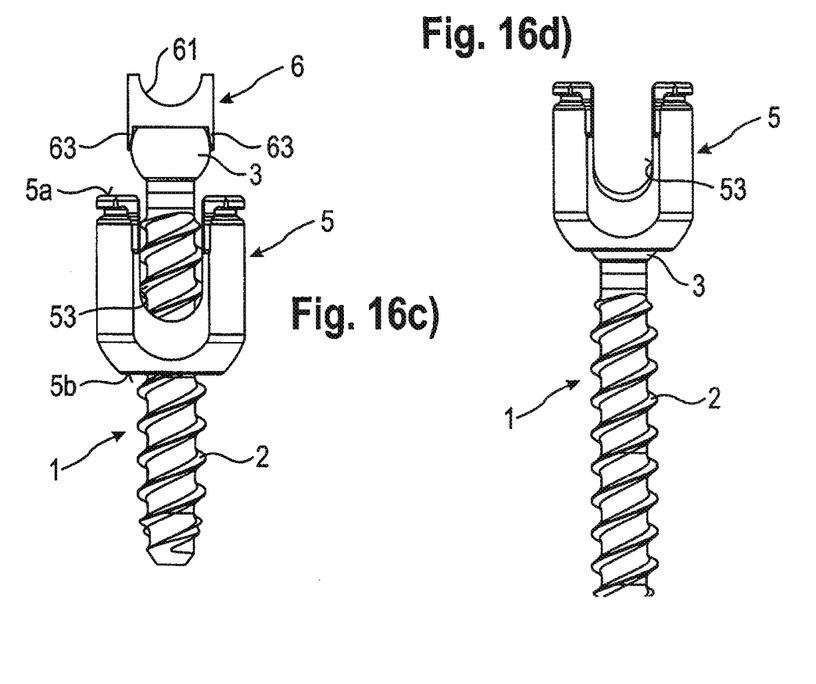

In use, the bone anchoring device may be delivered in a pre-assembled condition as shown in FIG. 16d). Usually, several bone anchoring devices are necessary. The screw members are then screwed into the bone or a vertebra and then the receiving parts are aligned to have the correct orientation for the insertion of the rod 100. Since the head is temporarily clamped, for pivoting the receiving parts it is necessary to apply a force to overcome the clamping force until each receiving part has the correct orientation. When all receiving parts are aligned, the rod, that connects the bone anchoring devices, is inserted and the inner screw 7 is tightened to move the pressure element downwards to lock the head so that the angular position of the screw member with respect to the receiving part is fixed. The rod is simultaneously fixed by the inner screw.

Figure 17:
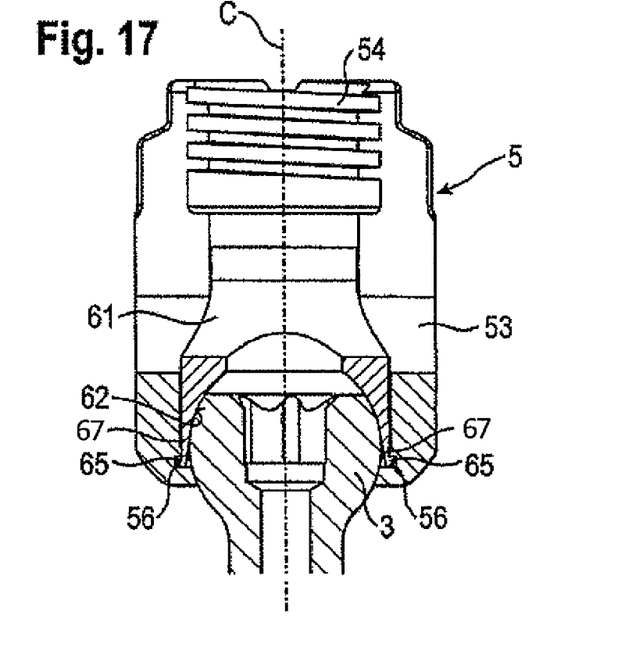
FIG. 17 shows a cross-sectional view of the polyaxial bone anchoring device according to a second embodiment, the section being taken in a plane including the rod axis.

A second embodiment of the polyaxial bone anchoring device is shown in FIG. 17. All parts that are the same as that of the previous embodiments are indicated with the same reference numerals and the description thereof is not repeated. The polyaxial anchoring device according to the second embodiment differs from the bone anchoring device according to the first embodiment in that the cylindrical edge 52a of the seat portion 52 may be not present. Instead of the hollow cylindrical edge 52a the receiving part has two recesses 56 in its inner wall that are offset from each other by 180° and oriented in the direction of the channel axis L. The location of the recesses is at a position nearer to the second end 5b than the greatest diameter E of the head 3 when the head 3 is inserted into the seat portion 52.

The pressure element comprises two additional lugs 67 that extend beyond the region with the greatest diameter E of the head and are oriented 90° each with respect to the lugs discussed above. Each of the lugs 67 has an outwardly extending nose 65. The nose 65 snaps into the recesses 56 when the screw member with the pressure element is inserted into the receiving part and provides an additional form fit connection between the receiving part and the pressure element. The recesses have such a height with respect to an axial direction that a further downward movement of the pressure element to lock the head 3 is possible.

Figure 18:
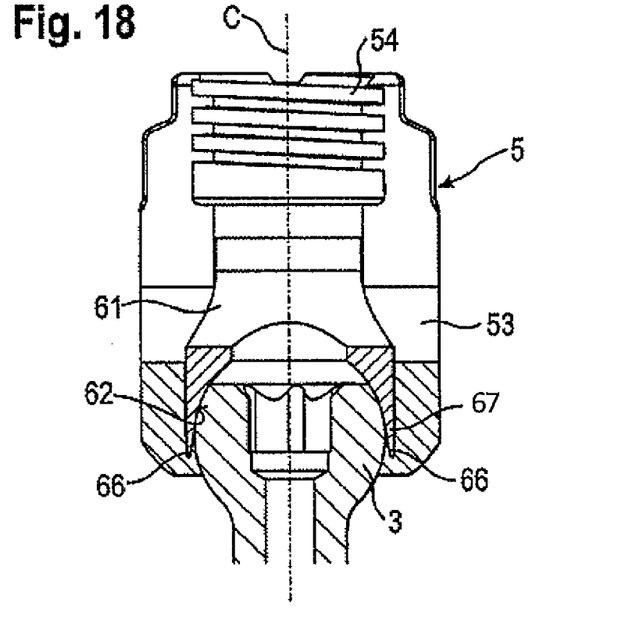
FIG. 18 shows a cross-sectional view of the polyaxial bone anchoring device according to a third embodiment, the section being taken along a plane including the rod axis.

A third embodiment of the polyaxial bone anchoring device is shown in FIG. 18. The polyaxial bone anchoring device according to the third embodiment differs from the bone anchoring device according to the second embodiment that instead of the recesses 56 and the noses 65 the lugs 67 have slightly outwardly extending flaps 66 that extend more outwardly than the inner diameter of the receiving part allows. When the head with the pressure element is inserted the flaps 66 press against the inner wall of the receiving part and additionally hold the head through a force-fit connection.

Modification of the previously described embodiments are conceivable. In a first modification, the head 3 is not held in the seat portion by an edge or by noses or flaps. In such a modification, in order to avoid a movement of the head with the pressure element in the direction towards the top end 5a, the pressure element is held by crimping within the receiving part.

Other modifications include more than two lugs or other shapes of the lugs as described with respect to the first embodiment. In further modifications, the lugs according to the first embodiment can be provided at other places than perpendicular to the channel axis. Also, the additional lugs and the noses of the second embodiment or the flaps of the third embodiment can be provided at other places or in other numbers.

The seat portion may have another shape than a spherical shape. For example, it can be tapered. All shapes that allow pivoting of the head like a ball and socket joint are possible. Also the head and the head contacting surface needs not to be spherical. It can be otherwise curved.

For the anchoring element all kinds of anchoring elements can be used and combined with a receiving part. These anchoring element are e.g. screws of different lengths, with different diameters, cannulated screws, screws with different thread forms, nails, etc. The head and the shaft can be separate parts that are connectable to each other.

Various kinds of receiving parts can be used in particular such with different locking devices. For example, instead of the one-part locking device such as the inner screw which locks the rod and the head simultaneously, a two-part locking device with an outer screw and an inner screw can be used. In this case, the pressure element has a U-shaped recess with legs extending above the rod. With the two-part locking device, the head and the rod can be fixed independently. Further, outer nuts, outer caps, bayonet locking devices or others are also possible. The shape of the receiving part is not limited to the embodiment shown. For example, the receiving part can have an asymmetric end portion for allowing a greater pivot angle of the screw member to a particular side.

In a further modification, the receiving part is configured to allow the introduction of the screw element from the bottom end.

The invention claimed is:

1. A polyaxial bone anchoring device comprising:
   an anchoring element having a shaft for anchoring in a bone, a head having a curved outer surface portion, and a longitudinal axis extending through the shaft and the head;
   a receiving part having a top end and a bottom end, a channel for receiving a rod therein, a coaxial bore extending from the top end in a direction of the bottom end, and a seat portion for receiving the head at the bottom end; and
   a pressure element configured to be arranged within the bore, the pressure element having a head contacting surface portion configured to contact at least a portion of the curved outer surface portion of the head having a greatest width or diameter in a direction perpendicular to the longitudinal axis of the anchoring element;
   wherein when the head and the pressure element are in the receiving part, the head is pivotable with respect to the receiving part and can be locked at an angle by exerting a downward pressure via the pressure element onto the head to press the head against the seat portion of the receiving part;
   wherein the greatest width or diameter of the head is greater than a greatest width or diameter of an inner space defined by the head contacting surface portion of the pressure element when the head contacting surface portion is unbiased, such that when the pressure element is in the receiving part and the head is fully inserted in the pressure element, the head biases the head contacting surface portion of the pressure element in a radially outward direction resulting in an interference fit wherein the head is not locked but is prevented from freely pivoting by friction; and
   wherein the head and the pressure element are movable relative to each other to a plurality of different angular positions, and the interference fit results at each of the plurality of different angular positions before locking the head in the receiving part.

2. The polyaxial bone anchoring device of claim 1, wherein the seat portion has a recess to accommodate the head contacting surface portion of the pressure element.

3. The polyaxial bone anchoring device of claim 1, wherein the head contacting surface portion of the pressure element comprises at least two distinct portions spaced apart from one another for clamping the head from opposite sides.

4. The polyaxial bone anchoring device of claim 3, wherein the distinct portions are formed as lugs or projections.

5. The polyaxial bone anchoring device of claim 1, wherein the pressure element is substantially cylindrical and has an upper end, a lower end, and a recess at the lower end, wherein the head contacting surface portion is at the lower end.

6. The polyaxial bone anchoring device of claim 1, wherein the receiving part is configured to hold the head at the seat portion and to prevent movement of the head towards the top end of the receiving part.

7. The polyaxial bone anchoring device of claim 1, wherein the seat portion comprises an upper edge defining an opening having a greatest width or diameter that is less than the greatest width or diameter of the head, and wherein when the head is at the seat portion, the upper edge is positioned closer to the top end of the receiving part than the portion of the head having the greatest width or diameter to prevent movement of the head towards the top end.

8. The polyaxial bone anchoring device of claim 1, wherein the pressure element comprises a spring element configured to snap into a recess at an inner wall of the receiving part, such that when the head and the pressure element are in the receiving part and the spring element is snapped into the recess, movement of the head towards the top end of the receiving part is prevented.

9. The polyaxial bone anchoring device of claim 1, wherein the head contacting surface portion comprises a flap that is oversized compared to an inner wall of the receiving part and is configured to achieve an interference fit with the inner wall of the receiving part to prevent movement of the head towards the top end of the receiving part when the head and the pressure element are in the receiving part.

10. The polyaxial bone anchoring device of claim 1, wherein the pressure element has a channel for receiving a rod.

11. The polyaxial bone anchoring device of claim 1, wherein the outer surface portion of the head is spherical.

12. The polyaxial bone anchoring device of claim 1, wherein the head contacting surface portion is spherical.

13. The polyaxial bone anchoring device of claim 1, wherein the seat portion is spherical.

14. The polyaxial bone anchoring device of claim 1, further comprising a fixation device configured to cooperate with the receiving part to lock the head in the seat portion and to fix a rod in the channel.

15. A method of coupling a rod to a bone via a polyaxial bone anchoring device, the bone anchoring device comprising an anchoring element having a shaft for anchoring in a bone, a head having a curved outer surface portion, and a longitudinal axis extending through the shaft and the head, a receiving part having a top end and a bottom end, a channel for receiving a rod, a coaxial bore extending from the top end in a direction of the bottom end, and a seat portion for receiving the head at the bottom end, a pressure element having a head contacting surface portion configured to contact at least a portion of the curved outer surface portion of the head having a greatest width or diameter in a direction perpendicular to the longitudinal axis of the anchoring element, wherein the greatest width or diameter of the head is greater than a greatest width or diameter of an inner space defined by the head contacting surface portion of the pressure element when the head contacting surface portion is unbiased, the method comprising:

inserting the bone anchoring device into a bone when the head is at the seat portion in the receiving part and is fully inserted in the pressure element, such that the head biases the head contacting surface portion of the pressure element in a radially outward direction resulting in an interference fit wherein the head is not locked but is prevented from freely pivoting by friction;

applying a force onto the receiving part or the anchoring element that is greater than a force of the friction to adjust an angular position between the anchoring element and the receiving part to one of a plurality of different angular positions, and the interference fit results at each of the different angular positions;

inserting a rod into the channel; and advancing a fixation device into the channel to push the rod against the pressure element, the pressure element against the head, and the head against the seat portion of the receiving part to lock the angular position between the bone anchoring element and the receiving part.

16. The method of claim 15, wherein prior to inserting the bone anchoring device into the bone, the method further comprises:

engaging the head and the pressure element such that the head contacting surface portion of the pressure element contacts the curved outer surface portion of the head; and inserting the head and the pressure element into the receiving part such that the head is at the seat portion.

17. The method of claim 16, wherein the head and the pressure element are engaged prior to inserting the head and the pressure element into the receiving part.

18. The method of claim 16, wherein the head and the pressure element are engaged after inserting the head and the pressure element into the receiving part.

19. The method of claim 16, wherein when the head and the pressure element are engaged and the head is at the seat portion, the head and the pressure element are prevented from moving towards the top end of the receiving part.

\* \* \* \* \*